US00PP35056P2

(12) United States Plant Patent
Smith

(10) Patent No.: US PP35,056 P2
(45) Date of Patent: Mar. 21, 2023

(54) ***CHRYSANTHEMUM* PLANT NAMED 'CIFZ0098'**

(50) Latin Name: ***Chrysanthemum* x *morifolium***
Varietal Denomination: 'CIFZ0098'

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/580,792

(22) Filed: Jan. 21, 2022

(51) Int. Cl.
*A01H 5/02* (2018.01)
*A01H 6/14* (2018.01)

(52) U.S. Cl.
USPC ..... Plt./292
CPC ..... *A01H 6/1424* (2018.05)

(58) Field of Classification Search
USPC ..... Plt./292
CPC ..... A01H 6/1424
See application file for complete search history.

*Primary Examiner* — Anne Marie Grunberg
(74) *Attorney, Agent, or Firm* — Dale Skalla

(57) ABSTRACT

A new garden type *Chrysanthemum* plant named 'CIFZ0098' particularly distinguished by its medium size plant with mound plant habit, medium sized decorative flowers with dark lavender/pink flower color, and a natural season response late September/early October.

1 Drawing Sheet

Figure 1:
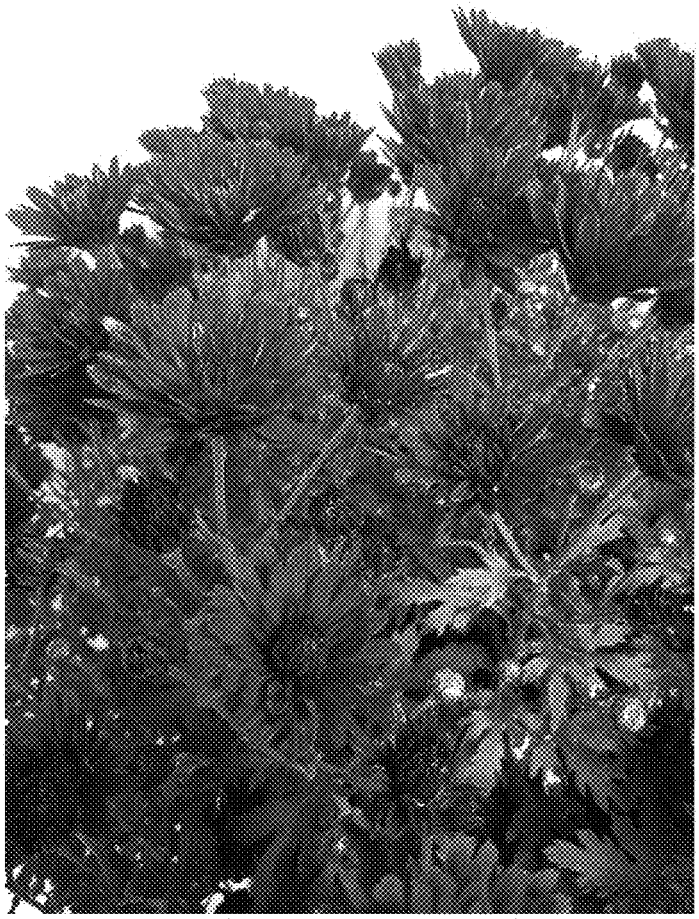

Latin name of the genus and species of the plant claimed: *Chrysanthemum* x *morifolium*.

Varietal denomination: 'CIFZ0098'.

BACKGROUND OF THE NEW PLANT

The present invention comprises a new *Chrysanthemum*, botanically known as *Chrysanthemum* x *morifolium*, and hereinafter referred to by the variety name 'CIFZ0098'.

'CIFZ0098' is a product of a planned breeding program. The new cultivar has medium size plant with mound plant habit, medium sized decorative flowers with dark lavender/pink flower color, and a natural season response late September/early October.

'CIFZ0098' originated from a cross made in October 2017 in Enkhuizen, The Netherlands. Seeds were sown in June 2018 in Gilroy, Calif. and 'CIFZ0098' was selected from the resulting population on Nov. 26, 2018 in Alva, Fla.

The female parent was an unnamed proprietary seedling '13-M241'.

TABLE 1

Characteristics of the female parent, compared to 'CIFZ0098':

| Trait | 'CIFZ0098' | '13-M241' |
|---|---|---|
| Natural response: | 1.5 weeks faster | 1.5 weeks slower |
| Blackcloth response: | ½ week slower | ½ week faster |
| Flower size: | Smaller | Larger |
| Flower color: | Dark pink/lavender | Red |
| Flower type: | Similar | Similar |
| Plant size: | Larger | Smaller |
| Flowering uniformity: | More uniform | Less uniform |

The male parent was an unnamed proprietary seedling '14-M539'.

TABLE 2

Characteristics of the male parent, compared to CIFZ0098':

| Trait | 'CIFZ0098' | '14-M539' |
|---|---|---|
| Natural response: | 4 weeks slower | 4 weeks faster |
| Flower size: | Smaller | Larger |
| Flower color: | Darker, no bicolor | Lighter, bicolor |
| Flower type: | Less disc florets | More disc florets |
| Plant size: | Larger | Smaller |
| Plant habit: | Similar | Similar |
| Flowering uniformity: | Less uniform | More uniform |

The first act of asexual reproduction of 'CIFZ0098' was accomplished when vegetative stem cuttings were propagated from the initial selection in January 2019 in Alva, Fla.

BRIEF SUMMARY OF INVENTION

Horticultural examination of plants grown from cuttings of the plant initiated in January 2019 and continuing thereafter, has demonstrated that the combination of characteristics as herein disclosed for 'CIFZ0098' are firmly fixed and are retained through successive generations of asexual reproduction.

'CIFZ0098' has not been observed under all possible environmental conditions. The phenotype may vary significantly with variations in environment such as temperature, light intensity and day length.

A Plant Breeder's Right for this cultivar has not yet been applied for. 'CIFZ0098' has not been made publicly available prior to the effective filing date of this application, notwithstanding any disclosure that may have been made less than one year prior to the effective filing date of this application by the inventor or another who obtained 'CIFZ0098' directly from the inventor.

The following traits have been repeatedly observed and are determined to be basic characteristics of the new variety.

The combination of these characteristics distinguishes this *Chrysanthemum* as a new and distinct variety.

BRIEF DESCRIPTION OF THE PHOTOGRAPHS

The accompanying photographic drawings shows typical flower and foliage characteristics of 'CIFZ0098' with colors being as true as possible with an illustration of this type. The photographic drawings show in FIG. 1 a close view of flower of the new variety and in FIG. 2 a flowering plant from an outdoor trial.

Figure 2:
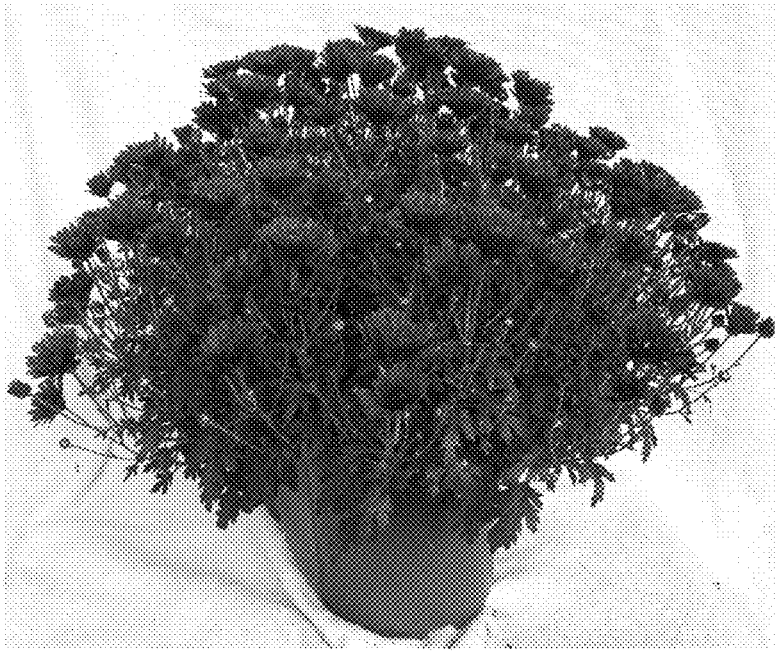

The aforementioned photographs: FIG. 1, as well as FIG. 2 were taken on Sep. 13, 2021 both showing a plant from the same blackcloth outdoor trial in Enkhuizen, The Netherlands.

These plants were about 14 weeks of age. One rooted cutting per pot had been planted in a 19 cm pot, not pinched in week 23, 2021 and black clothed from week 29. Plants started flowering the end of August 2021.

The measurements were taken in Enkhuizen, The Netherlands, in September 2021 on plants from the same outdoor blackcloth trial.

DETAILED BOTANICAL DESCRIPTION

Color references are made to The Royal Horticultural Society Colour Chart (R.H.S.) 2001.

DIFFERENCES BETWEEN THE NEW VARIETY 'CIFZ0098' AND TWO MOST SIMILAR VARIETIES

TABLE 3

| Trait | 'CIFZ0098' | 'Regal Yocheryl', U.S. Plant Pat. No. 13,974 |
|---|---|---|
| Natural response: | Similar | Similar |
| Blackcloth response: | 1 week slower | 1 week faster |
| Flower size: | Similar | Similar |
| Flower color: | Darker | Lighter |
| Flower type: | Similar | Similar |
| Plant size: | Bit larger | Bit smaller |
| Foliage: | Regular green | Dark green |
| Flowering uniformity: | More uniform | Less uniform |

TABLE 4

| Trait | 'CIFZ0098' | 'Zanmupizza', U.S. Plant Pat. No. 26,511 |
|---|---|---|
| Natural response: | Similar | Similar |
| Blackcloth response: | ½ week slower | ½ week faster |
| Flower size: | Larger | Smaller |
| Flower color: | Similar | Similar |
| Flower type: | Similar | Similar |
| Plant size: | Similar | Similar |
| Plant habit: | Less lumpy | More lumpy |
| Flower color longevity: | Less fade | More fade |
| Frost damage: | Less damage from frost | More damage from frost |

Plant:

*Form, growth and habit.*—Herbaceous garden-type, stems Upright and outwardly spreading, freely branching, strong and moderately vigorous growth habit.

*Plant height* (*above soil*).—28 cm.

*Plant height* (*inflorescence included*).—30 cm.

*Plant width.*—49 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

*Arrangement.*—Alternate.

*Immature leaf, color upper surface.*—RHS 137A.

*Immature leaf, color lower surface.*—RHS 138A.

*Mature leaf, color, upper surface.*—RHS 139A.

*Mature leaf, color lower surface.*—RHS 137A.

*Length.*—8.5 cm.

*Width.*—4.0 cm.

*Shape.*—Ovate, with distinct lobes.

*Base shape.*—Attenuate.

*Apex shape.*—Apiculate.

*Margin.*—4-lobed.

*Number of margin indentations.*—Approximately 34.

*Depth of margin indentations.*—0.4-0.6 cm.

*Leaf length terminal lobe relative to total leaf length.*—1:2.

*Leaf depth lower lateral sinus.*—1.5-2.4 cm.

*Texture, upper surface.*—Bifid hairs.

*Texture, lower surface.*—Bifid hairs.

*Color of veins, upper surface.*—RHS 138B.

*Color of veins, lower surface.*—RHS 138B.

*Pattern of veining.*—Palmate.

*Petiole color.*—RHS 138B.

*Petiole length.*—2.0-2.5 cm.

*Diameter.*—0.3 cm.

*Texture.*—Bifid hairs.

*Presence of stipules.*—Occasionally.

*If present, size of stipules.*—Tiny, up to 0.1 cm long and wide.

*Color of stipule.*—RHS 139A.

Stem:

*Quantity of main branches per plant.*—8.

*Color of stem.*—RHS 138A.

*Length of stem.*—9.0-10.0 cm.

*Diameter.*—0.5 cm.

*Length of internodes.*—1.0-1.5 cm.

*Texture.*—Bifid hairs.

*Color of peduncle.*—RHS 138B.

*Length of peduncle.*—4.0-6.0 cm.

*Peduncle diameter.*—0.2 cm.

*Texture.*—Bifid hairs.

Inflorescence:

*Type.*—Compositae, solitary, double, occasionally decorative type inflorescences borne terminally above foliage, ligulate ray florets arranged in whorls on a capitulum giving a decorative flower with some disc florets in the center of the flower and between ray florets.

*Quantity of short days to flowering* (*response time*).—Approximately 8 weeks.

*Quantity of inflorescences per plant.*—210 with some small buds developing.

*Lastingness of individual blooms on the plant.*—About four weeks from first color.

*Fragrance.*—Slightly spicy.

Bud (when showing color):
*Color*.—RHS N79C.
*Length*.—1.2 cm.
*Width*.—0.9 cm.
*Shape*.—Oblate.

Immature inflorescence (at moment of opening):
*Diameter*.—2.1 cm.
*Color of ray florets, upper surface*.—RHS N79C.
*Color of ray florets, lower surface*.—RHS N79C.

Mature inflorescence:
*Diameter*.—4.0 cm.
*Depth*.—2.5 cm.
*Total diameter of disc*.—0.0 to 0.5 cm.
*Receptacle color*.—RHS 137B.
*Receptacle height*.—0.6 cm.
*Receptacle diameter*.—1.2 cm.
*Length of corolla tube*.—0.1 cm.

Ray florets:
*Average quantity of florets*.—115 in several whorls.
*Color of florets, upper surface*.—RHS 71A.
*Color lower surface*.—RHS 72B.
*Length*.—2.1 cm.
*Width/diameter*.—0.4 cm.
*Shape*.—Oval.
*Apex shape*.—Tridentate.
*Base shape*.—Tube.
*Margin*.—Entire. Small incisions may be present at tip.
*Margin*.—Type of rolling — Weakly involute.
*Texture, upper surface*.—Papillate.
*Lower surface*.—Papillate.
*Ribs present*.—Yes.
*Number of keels*.—1.
*Profile at widest point*.—Weakly convex.
*Longitudinal axis shape*.—Incurving.
*Longitudinal axis curvature strength*.—Weak.
*Corolla tube shape*.—Flattened.

Disc florets:
*Number of disc florets*.—Up to 30, in center of flower but also a few between ray florets.
*Width*.—0.1 cm.
*Length*.—1.2 cm.
*Colour*.—RHS 9A.

Inflorescence (at moment of senescence):
*Color of ray florets, upper surface*.—RHS 72A.
*Color of ray florets, lower surface*.—RHS 72B.

Phyllaries:
*Quantity*.—20-25.
*Color, upper surface*.—RHS 137C.
*Color, lower surface*.—RHS 137D.
*Length*.—0.6 cm.
*Width*.—0.1-0.2 cm.
*Shape*.—Lanceolate.
*Apex shape*.—Acute.
*Base*.—Fused.
*Margins*.—Entire.
*Texture, upper surface*.—Glabrous.
*Texture, lower surface*.—Canescent.

Reproductive organs:
*Pistil*.—One.
*Length*.—0.4 cm.
*Style color*.—RHS 3C.
*Style length*.—0.3 cm.
*Stigma color*.—RHS 3D.
*Stigma shape*.—Bi-parted.
*Ovary color*.—RHS 149D.
*Ovary length*.—0.2 cm.
*Ovary width*.—0.1 cm.

Androecium:
*Stamens*.—1, found on only disc florets.
*Color of filaments*.—RHS 157C.
*Length filaments*.—0.2 cm.
*Anther color*.—RHS 9A.
*Anther length*.—0.2 cm.
*Anther shape*.—Oval to club shaped.
*Color of pollen*.—RHS 9A.
*Pollen amount*.—Moderate.
*Fertility/seed set*.—Has not been determined to date.
*Disease/pest resistance*.—Has not been determined to date.
*Hardiness*.—Has not been determined to date.

What is claimed is:

1. A new and distinct variety of *Chrysanthemum* plant named 'CIFZ0098' substantially as illustrated and described herein.

* * * * *